(12) United States Patent
Klassen et al.

(10) Patent No.: US 7,419,825 B2
(45) Date of Patent: Sep. 2, 2008

(54) ISOLATION OF NEURAL STEM CELLS USING GANGLIOSIDES AND OTHER SURFACE MARKERS

(75) Inventors: Henry Klassen, Pasadena, CA (US); Michael Schwartz, Garden Grove, CA (US); Michael J. Young, Gloucester, MA (US)

(73) Assignee: Children's Hospital of Orange County, Orange, CA (US)

( * ) Notice: Subject to any disclaimer, the term of this patent is extended or adjusted under 35 U.S.C. 154(b) by 267 days.

(21) Appl. No.: 10/128,009

(22) Filed: Apr. 22, 2002

(65) Prior Publication Data
US 2003/0040023 A1 Feb. 27, 2003

Related U.S. Application Data

(60) Provisional application No. 60/285,407, filed on Apr. 20, 2001.

(51) Int. Cl.
C12N 5/00 (2006.01)
C12N 5/06 (2006.01)
C12N 5/08 (2006.01)

(52) U.S. Cl. .................. 435/325; 435/368; 435/354; 435/363; 435/365

(58) Field of Classification Search .................. 435/377, 435/375, 368, 325
See application file for complete search history.

(56) References Cited

U.S. PATENT DOCUMENTS

| | | | |
|---|---|---|---|
| 5,466,572 A * | 11/1995 | Sasaki et al. | ................. 435/2 |
| 5,824,489 A | 10/1998 | Anderson et al. | |
| 5,928,947 A | 7/1999 | Anderson et al. | |
| 6,596,523 B1 * | 7/2003 | Sasaki et al. | ............... 435/193 |
| 2006/0099651 A1 | 5/2006 | Uchida et al. | |

OTHER PUBLICATIONS

Janeway et al., 2001, Immunobiology: the immune system in health and disease, Garland Publishing. Appendix II, pp. 1-3.*
Liepelt et al., Brain Res Dev Brain Res. Feb. 1, 1990;51(2):267-278.*
Marmur et al., Dev. Biol. Dec. 15, 1998;204(2):577-591.*
Morrisson et al., Cell. Mar. 5, 1999; 96(5):737-749.*
Pomeranz et al., Developmental Biology, 156:341-361 (1993).*
Allendoerfer, K. L., et al. (1995) FORSE-1, an Antibody That Labels Regionally Restricted Subpopulations of Progenitor Cells in the Embryonic Central Nervous System, Recognizes the Le[x] Carbohydrate on a Proteoglycan and Two Glycolipid Antigens. Mol. Cell. Neurosci. 6:381-395.
Berger, F., et al. (1998) Nicotinic Receptor-Induced Apoptotic Cell Death of Hippocampal Progenitor Cells. J. Neurosci. 18(17):6871-6881.
Claas, C., et al. (2001) Evaluation of Prototype Transmembrane 4 Superfamily Protein Complexes and Their Relation to Lipid Rafts. J. Biol. Chem. 276(11):7974-7984.
Dominguez, M., et al. (1998) Multiple functions of the EGF receptor in Drosophila eye development. Curr. Biol. 8:1039-1048.
Huh, G. S., et al. (2000) Functional Requirement for Class I MHC in CNS Development and Plasticity. Science 290:2155-2159.
Kim, S. U., et al. (1986) Neuroimmunology of Gangliosides in Human Neurons and Glial Cells in Culture. J. Neurosci. Res. 15(3):303-321.
Klassen, H. (2001) Surface markers expressed by multipotent human and mouse neural progenitor cells include tetraspanins and non-protein epitopes. Neurosci. Letters 312:180-182.
Kreidberg, J. A. (2000) Functions of $\alpha 3 \beta 1$ integrin. Curr. Opin. Cell Biol. 12:548-553.
Lillien, L. and Ralphael, H. (2000) BMP and FGF regulate the development of EGF-responsive neural progenitor cells. Development 127:4993-5005.
McLaren, F. H., et al. (2001) Analysis of neural stem cells by flow cytometry: cellular differentiation modifies patterns of MHC expression. J. Neuroimmunol. 112:35-46.
Mehler, M. F., et al. (2000) Developmental Changes in Progenitor Cell Responsiveness to Bone Morphogenetic Proteins Differentially Modulate Progressive CNS Lineage Fate. Dev. Neurosci. 22:74-85.
Morrison, S. J., et al. (1999) Prospective Identification, Isolation by Flow Cytometry, and In Vivo Self-Renewal of Multipotent Mammalian Neural Crest Stem Cells.Cell 96:737-749.
Odintsova, E., et al. (2000) Attenuation of EGF receptor signaling by a metastasis suppressor, the tetraspanin CD82/KAI-1. Curr. Biol. 10:1009-1012.
Okabe, M., et al. (1997) FEBS Letters 407:313-319.
Piper, D. R., et al. (2000) Immunocytochemical and Physiological Characterization of a Population of Cultured Human Neural Precursors. J. Neurophysiol. 84:534-548.
Hulspas, R. and Quesenberry, P. J., et al. (2000) Characterization of Neurosphere Cell Phenotypes by Flow Cytometry. Cytometry 40:245-250.
Reynolds, B. A. and Weiss, S. (1992) Generations of Neurons and Astrocytes from Isolated Cells of the Adult Mammalian Central Nervous System. Science 255:1707-1710.
Shatos, M. A., et al. (2001) Multipotent Stem Cells from the Brain and Retina of Green Mice. J. Regen. Med. 2:13-15.

(Continued)

Primary Examiner—Manjunath Rao
Assistant Examiner—Daniel C Gamett
(74) Attorney, Agent, or Firm—Knobbe Martens Olson & Bear LLP

(57) ABSTRACT

During the growth and study of NSCs, a range of molecules present on the surface of multipotent neural stem and progenitor cells (NSCs) were identified. These markers were identified using a number of human and murine neural stem cell lines, including retinal stem cells (RSCs). The NSC-specific markers identified included gene products as well as non-protein molecules and sugar epitopes not directly coded in the genome. Together with surface markers which were determined to be absent from the surface of hNSCs, the molecules described herein provide a means to enrich for neural stem cells, or neural progenitor cell subpopulations, particularly using combinatorial cell sorting strategies. These same molecules also represent targets for pharmacological manipulation of NSC populations and subpopulations, both in vivo and ex vivo. Furthermore, these molecules provide potential targets for therapeutic manipulation of other neural precursor-related cell types including malignant cell types as well as diseases originating from, or preferentially affecting, various uncommitted or replication-competent cell types.

7 Claims, 12 Drawing Sheets

OTHER PUBLICATIONS

Tiwari-Woodruff, S. K., et al. (2001) OSP/Claudin-11 Forms a Complex with a Novel Member of the Tetraspanin Super Family and β1 Integrin and Regulates Proliferation and Migration of Oligodendrocytes. J. Cell Biol. 153:295-305.

Uchida, N., et al. (2000) Direct isolation of human central nervous system stem cells. PNAS 97(26):14720-14725.

Zhang, S. C., et al. (1998) Generation of oligodendrolglial progenitors from neural stem cells. J. Neurocytol. 27:475-489.

Schulz, T.C. et al., "Directed neuronal differentiation of human embryonic stem cells" BMC Neuroscience 4(24):1-13 (Oct. 2003).

Mizumoto, H., et al., (2001) *Transplantation of Human Neural Progenitor Cells to the Vitreous Cavity of the Royal College of Surgeons Rat*. Cell Transplantation, vol. 10, pp. 223-233.

Bhattacharya S. et al. (2001) "Prospective identification and enrichment of ocular neural stem cells" IOVS 42(4): S197.

Kaneko, Y. et al. (2000) "Musashi1: an evolutionarily conserved marker for cns progenitor cells including neural stem cells" Developmental Neuroscience 22:139-153.

Supplementary Partial European Search Report from co-pending European Patent Application No. EP 02 73 1460, dated Jul. 20, 2005.

* cited by examiner

Isotype

GD2 ganglioside

CD9 tetraspanin

CD15 Lewis X (lacto-N-fucopentose III)

CD81 tetraspanin

| | File: CM + HNSC 02.20.01.004 | | | Sample ID: CM + HNSC 02.20.01 | |
|---|---|---|---|---|---|
| | Acquisition Date: 20-Feb-01 | | | Gate: No Gate | |
| Region | Events | % Gated | % Total | X Mean | Y Mean |
| R1 | 16447 | 80.07 | 80.07 | 587.91 | 388.25 |
| R2 | 3963 | 19.29 | 19.29 | 834.45 | 1.91 |
| R3 | 11022 | 53.66 | 53.66 | 499.04 | 553.96 |

| | File: CM + HNSC 02.20.01.004 | | | Sample ID: CM + HNSC 02.20.01 | |
|---|---|---|---|---|---|
| | Acquisition Date: 20-Feb-01 | | | Gate: G4 (R1 and R2) | |
| Region | Events | % Gated | % Total | X Mean | Y Mean |
| R1 | 3607 | 100.00 | 17.56 | 1589.10 | 540.33 |
| R2 | 3607 | 100.00 | 17.56 | 1589.10 | 540.33 |
| R3 | 0 | 0.00 | 0.00 | *** | *** |
| R4 | 3351 | 92.90 | 16.31 | 1686.50 | 569.17 |
| R5 | 207 | 5.74 | 1.01 | 33.15 | 21.95 |

| | File: CM + HNSC 02.20.01.004 | | | Sample ID: CM + HNSC 02.20.01 | |
|---|---|---|---|---|---|
| | Acquisition Date: 20-Feb-01 | | | Gate: G5 (R1 and R3) | |
| Region | Events | % Gated | % Total | X Mean | Y Mean |
| R1 | 10649 | 100.00 | 51.85 | 37.37 | 10.40 |
| R2 | 0 | 0.00 | 0.00 | *** | *** |
| R3 | 10649 | 100.00 | 51.85 | 37.37 | 10.40 |
| R4 | 114 | 1.07 | 0.56 | 1170.54 | 339.60 |
| R5 | 10424 | 97.89 | 50.75 | 21.08 | 6.36 |

File: CM 02.20.01.004     Sample ID: CM 02.20.01
Acquisition Date: 20-Feb-01     Gate: No Gate

| Quad | Events | % Gated | % Total | X Mean | Y Mean |
|---|---|---|---|---|---|
| UL | 1 | 0.01 | 0.01 | 2.29 | 98.22 |
| UR | 126 | 1.14 | 1.14 | 1763.87 | 460.95 |
| LL | 10501 | 95.07 | 95.07 | 4.42 | 2.19 |
| LR | 418 | 3.78 | 3.78 | 64.29 | 19.45 |

File: HNSC 02.20.01.004     Sample ID: HNSC 02.20.01
Acquisition Date: 20-Feb-01     Gate: No Gate

| Quad | Events | % Gated | % Total | X Mean | Y Mean |
|---|---|---|---|---|---|
| UL | 102 | 1.01 | 1.01 | 12.94 | 423.54 |
| UR | 7632 | 75.21 | 75.21 | 1257.37 | 487.97 |
| LL | 1119 | 11.03 | 11.03 | 6.34 | 4.29 |
| LR | 1295 | 12.76 | 12.76 | 99.65 | 31.84 |

| Region | Events | % Gated | % Total |
|---|---|---|---|
| R1 | 3792 | 10.90 | 10.90 |

| Region | Events | % Gated | % Total |
|---|---|---|---|
| R1 | 150 | 71.43 | 71.43 |

ISOLATION OF NEURAL STEM CELLS USING GANGLIOSIDES AND OTHER SURFACE MARKERS

RELATED APPLICATION

This application claims priority under 35 U.S.C. § 119(e) to U.S. Provisional Application 60/285,407, filed Apr. 20, 2001.

FIELD OF THE INVENTION

The present invention relates generally to the isolation of neural stem cells. More specifically, the present invention relates to a method of using gangliosides and other markers to isolate neural stem cells from the central nervous system, including brain, spinal cord, and retina.

BACKGROUND OF THE INVENTION

Cell transplantation has over the last two decades emerged as a promising approach for restoration of function in neurodegenerative diseases, in particular Parkinson's and Huntington's disease. Clinical trials have so far focused on the use of implants of embryonic mesencephalic tissue containing already fate-committed dopaminergic neuroblasts with the capacity to develop into fully mature dopamine neurons in their new location in the host brain. A major limitation of the fetal cell transplantation procedure is the low survival rate of the grafted neurons (in the range of 5-20%) which makes it difficult to obtain sufficient cells for grafting in patients. Currently, mesencephalic fragments from at least 6-8 embryos are needed for transplantation in one Parkinson's disease patient. Moreover, the ethical, practical and safety issues associated with the use of tissue from aborted human fetuses are problematic, and severely restrict the possibility for applying the procedure outside highly specialized centers.

It was recently demonstrated that immature neural progenitor cells with multipotent properties, called neural stem cells (NSCs), can be isolated from both the developing and adult CNS. Neural stem cells are multipotent cells which can be differentiated into any type of neural cell, including neurons, astrocytes, glia and oligodendrocytes. The successful propagation of mammalian neural stem cells (NSC) in culture, first reported by Reynolds and Weiss (1992), has opened up hitherto unforeseen opportunities in the field of neural transplantation and, therefore, harvesting these cells from donated adult human tissue is of great interest.

However, it would be advantageous to isolate the NSCs from the other cells in the brain or enrich them such that the purest population of multipotent cells possible can be obtained. One favored strategy for cell isolation is the identification of target epitopes on the surface of NSCs accessible to monoclonal antibodies. These antibodies can then be selectively tagged, e.g., with a fluorescent label, whereupon selecting for the tagged antibody results in selection of the cell on which it is bound. If the target molecule is expressed only by the desired cell type, very high levels of enrichment are possible. The problem with this strategy is that of identifying the target epitopes which will isolate the NSCs, allow for specificity of attachment and will not activate cellular processes.

The identification and enrichment using specific cell surface markers has been used previously in the isolation of another type of stem cell, neural crest stem cells (NCSC's) (Anderson and Stemple, 1998, U.S. Pat. No. 5,824,489). However, the use of the method in the isolation of neural stem cells (NSCs) has been slow to develop, possibly due to the difficulty in identifying NSC-specific markers. Uchida et al., 2000, describes a method for the isolation of NSCs using a specific epitope. In this work, the authors restrict their definition of human neural stem cells to those cells within the human brain which are CD133+/CD34− (and CD24−/lo) and describe the use of this marker profile to isolate NSCs. They also state that the CD133+/CD34− (and CD24−/lo) fraction alone contains neural stem cells because neurospheres could not be generated from the CD133− fraction. However, there are a number of problems and inconsistencies with this method. For example, the authors state that neurospheres could not be generated from the CD133− population. However, the population and method of enriching may have produced variability in frequency of neurosphere initiating cells resulting from such manipulation. It is likely that the process of mincing, enzymatically-dissociating, and sorting the cells twice, increased levels of damage to constituent cells, leaving a number of the cells non-viable.

Embryonic stem cells have been shown to be useful for transplantation treatment of a number of diseases. Since 1987, about 250 patients with advanced Parkinson's Disease have received transplants of mesencephalic dopamine neurons, obtained from 6-9 week old cadaver embryos at several centers in Europe and America. There is now convincing data to show that embryonic human nigral neurons, taken at a stage of development when they have started to express their dopaminergic phenotype, can survive, integrate and function over a long time in the human brain (i.e. in a tissue environment with an ongoing disease process). Embryonic stem cells are very primitive, non-neuronal cells which can be induced to differentiate into neural progenitor cells by the treatment with specific morphogens. Thus, there is reason to believe that neural progenitors or neural stem cells (NSCs) could be used for the same purpose. For example, neural stem cells were shown to be useful for the treatment of hypoxic-ischemic (HI) brain injury (stroke). When NSCs were injected into mice brains subjected to focal HI injury, they appeared to integrate appropriately into the degenerating central nervous system (CNS), and showed robust engraftment and foreign gene expression within the region of HI injury. They also appeared to have migrated preferentially to the site of ischemia, experienced limited proliferation, and differentiated into the neural cells that were lost to injury, trying to repopulate the damaged brain area. Therefore, the transplantation of exogenous NSCs may, in fact, augment a natural self repair process in which the damaged CNS "attempts" to mobilize its own pool of stem cells. Providing additional NSCs and trophic factors may optimize this response (Park, KI; 2000, Yonsei Med J, Dec;41(6):825-35). Therefore, NSCs may provide a novel approach to reconstituting brains damaged by HI brain injury as well as Parkinson's disease and other neurodegenerative disorders.

Because NSCs appear to be excellent candidates for restorative cell replacement and gene transfer therapies, and could eventually offer a powerful alternative to primary fetal CNS tissue in clinical transplantation protocols, methods for the successful isolation from adult brain are needed.

SUMMARY OF THE INVENTION

Previous methods for the isolation of neural stem cells (NSCs) using the cell marker CD133 have proved problematic, therefore, a method was developed which allows neural stem cells, human or otherwise, to be enriched without reference to CD133. In fact, completely different marker molecules were identified and used. Furthermore, in contrast to previous studies (Uchida, et al, 2000) it was shown that these neural progenitors are CD34+ and CD133−, suggesting that the previous method of identifying NSCs was flawed.

One embodiment is a method for enriching for neural stem cells or a more restricted subset of progenitors, by, identifying cells with at least one positive or negative neural stem cell-specific markers from a population of cells; and enriching for said cells with the at least one positive or negative neural stem cell-specific marker. In one embodiment, the positive or negative neural stem cell marker is selected from the group consisting of: proteinaceous or nonproteinaceous markers. In a further embodiment, the positive neural stem cell markers are proteinaceous and are selected from the group consisting of: CD9, CD15, CD95, CD3, MHC 1 and β2 microglobulin.

In one embodiment, the negative neural stem cell marker is proteinaceous and is selected from the group consisting of: MHC class II, HLA-DR, Glycophorin-A, CD3, CD5, CD7, CD 10, CD1 b, CD13, CD14, CD16, CD19, CD20, CD22, CD23, CD25, CD31, CD33, CD41, CD45, CD54, CD80, CD83, CD86, TAPA-1, CD15, CD95, CD9, MHC classI, β2 microglobulin, CD8, CD34, CD38, CD56, CD81, and CD152, CD133, CD117, CD154.

In a further embodiment, the positive neural stem cell marker is nonproteinaceous and is ganglioside GD2.

In one embodiment, the enriching for cells with neural stem cell-specific markers is by cell sorting. In a further embodiment, the enriching for cells with neural stem cell-specific markers is by at least one affinity column.

In one embodiment, the population of cells is from a tissue selected from the group consisting of: the brain, the spinal cord, the retina, and fetal tissue. Preferably, the brain and retina are adult brain and retina.

One embodiment is an enriched neuronal stem cell population enriched by the method above or by use of GD2 alone.

A further embodiment is a method of enriching for retinal stem cells, by: identifying cells which express the GD2 gangliosidic marker from a population of cells; and enriching for said cells which express the GD2 gangliosidic marker. In one embodiment, the population of cells is retinal tissue and fetal tissue.

A further embodiment is a method of testing for drugs which are agonists or antagonists of neural stem cells.

A further embodiment is a method for diagnosing and identifying neural tumors, by: identifying whether cells from said neural tumors express positive or negative neural stem cell markers. In one embodiment, the positive neural stem cell markers are selected from the group consisting of; Ganglioside GD2, TAPA-1, CD15, CD95, CD9, MHC classI, β2 microglobulin, CD8, CD34, CD38, CD56, CD81, and CD152.

In a further embodiment, the negative neural stem cell markers are selected from the group consisting of; MHC class II, HLA-DR, Glycophorin-A, CD3, CD5, CD7, CD10, CD11b, CD13, CD14, CD16, CD19, CD20, CD22, CD23, CD25, CD31, CD33, CD41, CD45, CD54, CD80, CD83, CD86, CD133, CD117, CD154.

A further embodiment is a method for controlling excessive proliferation of neural transplants, by: administering an agent which reduces the proliferation of neural transplant cells selected from the group consisting of: antibodies to neural stem cell markers, antisense oligonucleotides for neural stem cell markers, and antagonists of neural stem cell markers. In one embodiment, the neural stem cell markers are selected from the group consisting of: GD2, TAPA-1, CD 15, CD95, CD9, and CD15.

A further embodiment is a method for treating neural tumors, by: administering an agent which reduces the proliferation of neural transplant cells selected from the group consisting of: antibodies to neural stem cell markers, antisense oligonucleotides for neural stem cell markers, and antagonists of neural stem cell markers. In one embodiment, the neural stem cell markers are selected from the group consisting of: GD2, TAPA-1, and CD15.

A further embodiment is a method for the isolation of NSCs by: isolating tissue from a mammalian subject, treating said cells with a differentiation agent, and identifying cells which express MHC class I markers and/or peptides of internal cellular markers of NSCs. In one embodiment, the internal cellular markers of NSCs are selected from the group consisting of: Nestin, MASH I, and MSH I.

A further embodiment is a method for the isolation of RSCs by: isolating tissue from a mammalian subject, treating said cells with a differentiation agent; and identifying cells which express MHC class I markers and/or peptides of internal cellular markers of RSCs.

BRIEF DESCRIPTION OF THE DRAWINGS

FIGS. 1$a$-$i$ show data obtained using human cells (human neuronal progenitor from Clonetics), FIGS. 1$j$-$k$ using mouse cells. The mouse cells used were mouse brain and retina from a transgenic GFP mouse or mouse brain from a transgenic pNestin-GFP mouse. The GFP mouse expresses GFP in all cells, and the pNestin-GFP mouse expresses GFP only in brain. In each case the target molecule is shown as solid gray, the isotype control with a fine black outline. The disparity between target and isotype along the X-axis defines the intensity of the target signal. FIG. 1$a$ shows high intensity labeling for $G_{D2}$ ganglioside (gray solid line)—isotype control (fine outline), FIG. 1$b$ shows equally intense labeling for MHC class I (bold outline) and β-2 microglobulin (gray solid line)—isotype control (fine outline), FIG. 1$c$ shows high intensity labeling for CD81 (gray solid line)—isotype control (fine outline), FIG. 1$d$ shows high intensity labeling for CD56 (gray solid line)—isotype control (fine outline), FIG. 1$e$ shows moderately high intensity labeling for CD15 (Gray solid line)—isotype control (fine outline), FIG. 1$f$ shows moderately high intensity labeling for CD95 (Gray solid line)—isotype control (fine outline), FIG. 1$g$ shows moderately high intensity labeling for CD95 (Gray solid line)—isotype control (fine outline), FIG. 1$g$ shows moderately high intensity labeling for CD9 (Gray solid line)—isotype control (fine outline), FIG. 1$h$ shows moderate labeling for CD34 (Gray solid line)—isotype control (fine outline). FIG. 1$i$ shows a small subpopulation of hNSCs labeling for $G_{D3}$ ganglioside (Gray solid line)—isotype control (fine outline) over a broad range of intensities. FIG. 1$j$ shows $G_{D2}$ ganglioside labeling (Gray solid line)—isotype control (fine outline) on mouse brain-derived neural stem cells obtained from GFP-transgenic mice. FIG. 1$k$ shows $G_{D2}$ ganglioside labeling (Gray solid line)—isotype control (fine outline) on retinal stem cells also obtained from GFP-transgenic mice.

FIG. 3 depicts the influence of differentiating conditions on the expression of target molecules by hNSCs. In each case the target molecule is shown as solid gray, the isotype control with a fine black outline. The bold outline indicates the profile of the target molecule after hNSCs were cultured in fetal bovine serum (FBS).

FIG. 5e is β-2 microglobulin.

FIG. 6a is a histogram showing the bright endogenous FITC+fluorescence emitted by pNestin-GFP neural stem cells when cultured under standard proliferation conditions (20 ng/ml EGF). FIG. 6b illustrates a modest decrease in endogenous fluorescence (left shift) induced by 3 days of culture under differentiation conditions. FIG. 6c is the marked decrease in endogenous fluorescence induced by 7 days of differentiation.

FIG. 7a shows the profile for $G_{D2}$ ganglioside, FIG. 7b shows the profile for MHC antigen IA-d, FIG. 7c shows the profile for MHC antigen H2Kb.

FIG. 8 depict the use of anti-$G_{D2}$ ganglioside antibody during fluorescence-activated cell sorting (FACS) to effectively enrich for neural stem cells. Cultured hNSCs were combined with human apheresis product and mixture was labeled with anti-$G_{D2}$-FITC, CD56-PE and CD45 Pe-Cy5.

FIG. 9a shows whole brain homogenate which was incubated with anti-GD2 primary antibody and PE conjugated secondary antibody, then sorted by FACS to select for GD2+ cells. FIG. 9b depicts the initial GD2 population labeled R1 which was 10.9%. FIG. 9c depicts the resulting sorted population which was 71% GD2+ representing an enrichment of approximately 700%.

DETAILED DESCRIPTION OF THE PREFERRED EMBODIMENT

Figure 1A:
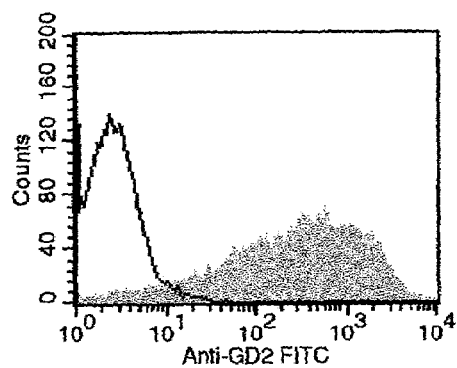
FIG. 1 depicts flow cytometric evidence for the presence of specific target molecules on the surface of NSCs.

The work herein identifies a range of molecules consistently present on or absent from the surface of multipotent neural stem and progenitor cells (NSCs) and in different subsets of NSCs and retinal stem cells RSCs. These molecules or markers were identified using a number of human and murine neural stem cell lines, including retinal stem cells (RSCs). The NSC-specific markers identified include gene products as well as non-protein molecules and sugar epitopes not directly coded in the genome. Together with surface markers which were determined to be absent from the surface of hNSCs, the molecules described herein provide a means to enrich for neural stem cells, or neural progenitor subpopulations, particularly using combinatorial cell sorting strategies. These same molecules also represent targets for pharmacological manipulation of NSC populations and subpopulations, both in vivo and ex vivo. Furthermore, these molecules provide potential targets for therapeutic manipulation of other neural precursor-related cell types including those that can be found in malignant conditions as well as other diseases originating from, or preferentially affecting, various uncommitted or replication-competent cell types.

Definitions

A "neural stem cell" as used herein is a neural progenitor cell which is proto-neuronal/proto glial. During development, embryonic stem cells which are very primitive totipotent cells are thought to pass through a neural stem cell stage as they are developing into neural cells. Neural stem cells can be induced to differentiate into any neural cells including glia, oligodendrocytes, neurons, or astrocytes. Cells were characterized as multipotent neural progenitor cells based on the ability to propagate over many passages, expression of nestin and Ki-67, proto-neuronal morphology, as well as the ability to differentiate into neurons and glia.

As used herein "embryonic stem cells" are totipotent cells isolated from embryonic or fetal tissue which may be treated with morphogens to differentiate into neural stem cells.

Neural Stem Cells (NSCs)

Neural stem cells are multipotent progenitor cells which can be found in adult brain and related tissue as well as embryonic tissue. When neural stem cells are contacted with certain factors permissive for neuronal and glial cell differentiation, such cells will differentiate into neurons, glia, oligodendrocytes and astrocytes. When NSCs are grown in the presence of fetal calf serum, or other morphogenic agents, they can be differentiated into these various cell types or less primitive stem cells.

Sources of NSCs may be any tissue known to one of skill in the art, including but not limited to: brain, spinal cord, fetal tissue, retina, and embryo.

NSC-Specific Markers

Because previous methods for the isolation of neural stem cells (NSCs) using the cellular marker CD133, proved problematic, a method was developed herein which allows neural stem cells, human or otherwise, to be enriched without reference to CD133. In fact, completely different marker molecules were identified and used herein. Furthermore, in contrast to previous studies (Uchida, et al, 2000) it was shown that some neural progenitors are CD133− and CD34+, suggesting that the previous method of identifying NSCs as CD133+CD34− was flawed.

For example, the method of Uchida et al., 2000, allows for the isolation of NSCs using the specific epitope CD133. In this work, the authors restricted their definition of human neural stem cells to those cells within the human brain which were CD133+/CD34− (and CD24−/lo) and described the use of this marker profile to isolate NSCs. They also stated that the CD133+/CD34− (and CD24−/lo) fraction alone contains neural stem cells because neurospheres could not be generated from the CD133− fraction. CD133 was previously thought to be a definitive marker of neural stem cells. However, the results herein show that it is in fact a negative marker.

Although this method appears to isolate a population of NSCs there are a number of problems with the method as well as inconsistencies in the data. For example, there is no data presented that the subset of cells that the authors describe as CD34−/CD133+ are in fact CD34 negative, suggesting that the NSCs isolated may be a mixed population. Also, CD133 (5F3) cells were artificially separated from a single population by sorting the cells at the CD133 expressing-end of the population on two separate occasions, then claiming, upon reanalysis, that two separate populations exist (their FIG. 1c). They use two CD133 clones (5F3), commercially available from Miltenyi Biotec, and infer that an antibody they developed against the same immunogen, CD 133 (5E12) clone, has similar properties. In a similar manner, they gate cells extending from a single population of cells in a two fluorescence dot plot, comparing the 5F3 CD133 and the 5E12 CD133 clones, which extend outward from the population at a 45 degree angle toward the upper right area of the plot. This type of pattern is a hallmark of non-specific binding, thus, also consistent with dead or dying cells (the authors mention that a viability dye, propidium iodide, was used but no evidence is presented). Comparison of single populations to a matched isotype control is not shown or mentioned. An isotype control is mentioned with regards to sort regions used to separate CD133+/CD24+ and CD133+/CD24− cells. However, these cells represent a small percentage of the CD133-expressing extreme of single CD24+ and CD24− fetal brain cells and thus could result from non-specific binding. When tissue is minced, enzymatically-dissociated, and sorted twice as is done to the NSC population from Uchida et al 2000, there is likely to be increased levels of damage to constituent cells. This fact may have contributed to the variability in frequency of neurosphere initiating cells resulting from such manipulation. No mention of statistical significance of neurosphere initiating cell frequency in the experiments relating to FIG. 2c, (n=8) is mentioned.

Thus, it is clear that a convincing method for isolating NSCs has not yet been developed, Uchida et al and other previous studies have focused on the neural stem cell markers which are protein in origin. However, it has long been appreciated that the cellular membranes of CNS neurons are a rich source of gangliosides. More recently it has been shown that these molecules are present during neural development in the membranes of cells of various lineages. These studies clearly demonstrated that gangliosides can rarely if ever be used as lineage-specific markers. Although less obvious, these complex ganglioside patterns are consistent with the behavior of neural stem/progenitor cells, which retain multipotency much further into the differentiation process than had hitherto been appreciated. Furthermore, there has been no prior evaluation of gangliosides in a neural stem/progenitor cell line, despite general appreciation of the abundance of gangliosides in a variety of neoplasms, particularly those of neuroepithelial origin. The studies herein provide a number of useful positive and negative NSC markers which are protein as well as ganglioside in origin.

Differentiation of NSCs

Many differentiation agents are known to one of skill in the art which can differentiate stem cells, retinal stem cells, or neural stem cells into specific types of nerve cells, retina cells or types of progenitors. Therefore, it is envisioned that the stem cells isolated herein may be differentiated by any means known to one of skill in the art. Some examples of differentiation agents, include, but are not limited to Interferon gamma, fetal calf serum, nerve growth factor, removal of EGF, removal of bFGF (or both), neurogenin, BDNF, thyroid hormone, BMPs, LIF, sonic hedgehog, GDNFs, VEGFs, interleukins, interferons, SCF, activins, inhibins, chemokines, retinoic acid and CNTF. The cells may be differentiated permanently or temporarily. For example, cells may be differentiated temporarily to express a specific marker, for example, in order to use that marker for identification. Then, the differentiation agent may be removed and the marker may no longer be expressed. However, it is to be understood that within the context of differentiation, agents such as interferon gamma, though inducing the expression of different markers, may not be classified as classical differentiation agents.

It is also to be understood that any anti-differentiation agents known to one of skill in the art may be used, including but not limited to: TGF-β, TGF-α, EGF, FGFs, and delta (notch ligand).

Uses of NSC Specific Markers

Although there are an extensive number of uses for NSC-specific markers, a few of the more common ones will be presented in more detail below. A major role of such markers involves enrichment of NSCs from a mixed population.

It is envisioned that the target molecules described herein are useful for the enrichment of neural stem cells when isolating these cells from any source, embryonic (fetal) brain or neural tissue or post-embryonic brain or spinal cord tissue. Preferably, a tissue homogenate derived from either surgical specimen or post-mortem donation is used as the source for isolating NSCs. In this way a large easily obtainable source of NSCs can be produced for use in further research or treatment of brain pathology.

In one embodiment, a method is used to identify neural stem cells wherein said method identifies said NSCs using at least one positive neural stem cell marker. In a further embodiment one positive and one negative marker is used. In another embodiment, more than one positive marker and more than one negative marker is used.

In a further embodiment, the positive and negative markers can be a "fingerprint" for identification of the NSCs. The positive and negative markers can be any identifiable marker. In one embodiment, the positive and negative markers are protein and/or carbohydrate (glycosidic).

In one embodiment, the positive markers are any one or more of the following: MHC I, β2-microglobulin, GD2 ganglioside, GD3 ganglioside (in some cases), CD8, CD9, CD15, CD34, CD38, CD56, CD81, CD95, and CD152. In a further embodiment, the positive markers are any one or more of the following: CD9, CD15, CD81, CD95, GD2, GD3, and CD34. In a further embodiment, the positive markers are selected from the group consisting of: CD15, CD81, CD95, and GD2. In a further embodiment, the positive markers are MHC I, MASH 1, MSI 1, and Nestin (MHC I or MHC II when induced). In a further embodiment, the positive markers are any one or more of MHCI and a peptidic fragment of MASH 1, MSI 1, or Nestin. In one embodiment, the antigen CD54 is tested before or after differentiation and cells which express it only after differentiation are isolated. In a further embodiment, Cells which express CD15 only before differentiation but not after are identified. In a further embodiment, cells which express CD34 before differentiation and more highly after differentiation are isolated.

In a further embodiment, the positive markers may be used alone and include, but are not limited to, GD2 and CD15. The tetraspanins (CD9 and CD81) may not work as well alone as a single marker, however, they may be very useful in combination with other positive or negative markers and may be useful for pharmaceutical intervention or to manipulate the cells which have already been isolated.

In a further embodiment, the MHC class I markers may be used for isolation alone or in combination with other markers. However, it is envisioned that the MHC class I markers may be useful as a potential marker to induce rejection of cells which are not behaving appropriately. For example, transplanted cells which are over-growing may be destroyed. The MHC class I markers are variably expressed on different subsets. However, in a subset which does not express them, they may be induced with agents such as interferon when necessary.

In one embodiment, the negative markers are any one or more of the following: MHC II, HLA-DR, Glycophorin-A, GD3 (positive in a very few cases), CD1a, CD3, CD5, CD7, CD10, CD11, CD13, CD14, CD16, CD19, CD20, CD22, CD23, CD25, CD31, CD33, CD41, CD45, CD54, CD80, CD83, CD86, CD133, CD117, and CD154. In a further embodiment, the negative markers are any one or more of the following: MHC class II, CD3 (TCRαβ-1), CD7, CD10, CD16, CD54. In a further embodimnt, the negative markers may be MHC class II and/or CD133.

The method of enrichment can be any method known to one of skill in the art which enriches for a population of cells using specific cell surface markers. For example, the method can be fluorescence-activated cell sorting (FACS), affinity columns, affinity beads, or any method which selectively binds the specific cell surface molecules. Alternatively, the method may use the cell surface molecules which are not expressed by NSCs to selectively remove or kill the undesirable cells, and, in this way, enrich for the desirable cells. Alternatively, the method can be with the use of magnetic beads which selectively bind the NSCs.

A further embodiment of the invention is the use of these specific cell surface markers/molecules to enrich for particular subpopulations of neural progenitor cells. For example, it is thought that the population of neural progenitor cells contains some totipotent cells which can differentiate into any neural cell type, some multipotent cells which can only differentiate into certain cell types, and some cells which have advanced further along the path of differentiation and may only be able to differentiate into one cell type. Therefore, it may be advantageous to enrich for a population of cells which is no longer able to differentiate into a particular type (i.e. glial cell) or which is only able to differentiate into one specific cell type (e.g. photoreceptors or dopaminergic neuron).

A further embodiment is the use of these positive and negative neural stem cell specific markers for identification of neural stem cells or of a subpopulation of neural stem cells which are associated with a disease or may be identified post-operatively during a cell transplantation.

A further embodiment is the use of the cell specific neural stem cell markers to identify and diagnose any cell, but particularly, cancer cells from a tumor or metastasis, which has a neural origin. This may have a relation to the course of treatment for the cancer. For example, typically, the less differentiated the cancer, the more invasive. Thus, a tumor which is composed of less differentiated cells may need to be treated more aggressively then one which is composed of more differentiated neural cells. Since neural stem cells are thought to represent one of the earliest cells in development, the more the presence or absence of specific neural stem cell markers (or "fingerprint") matches the cancer cell's "fingerprint", the more likely it is that the cancer cells are undifferentiated. In other words, if the cancer cell possesses the positive markers identified herein and does not have the negative markers, then it is a very undifferentiated cancer. The specific neural stem cell markers or proteins and enzymes important to their expression, can be identified in any way known to one of skill in the art, including FACS, cytometry, enzymatically, by Western blot and by PCR.

Research into Neuronal Cell Development:

A further embodiment is the use of the NSC cell surface markers, both positive and negative, to study stem and progenitor cell behavior during development and in maturity. For example, it is unclear whether cell development proceeds along a linear, temporal or branched progression. It is also unclear how important the effect of neighboring cells are to development and differentiation of the neural stem cells.

Use of Antisense Oligonucleotides and/or Antibodies to NSC-Specific Markers as Therapeutics:

One embodiment is the use of antisense oligonucleotides which specifically inhibit the expression of positive NSC-specific protein markers. The antisense oligonucleotide can be identified and synthesized using techniques known to one of skill in the art. In addition, variants may be produced using any bases known to one of skill in the art, including various well-known modified bases. It is envisioned that the antisense when acting on a positive NSC marker will inhibit the growth of NSCs or NSC-related cancer cells. Alternatively, the antisense oligonucleotides may specifically act on a negative NSC marker in an NSC or NSC-like cell. It is envisioned that when acting on a negative NSC marker in the right environment, the antisense oligonucleotide would increase the growth of an NSC or a less differentiated cell.

A further embodiment is the use of antibodies which specifically bind to positive NSC markers. It is envisioned that the antibodies would target, identify, or bind to the NSCs for treatment, enrichment or diagnosis. For example, antibodies to the NSC-specific markers could be used to target a therapeutic agent to the NSCs specifically. Alternatively, antibodies to negative NSC markers may be used to weed non-NSC cells from a population.

Alternatively, markers may be induced by the addition of cytokines or other agents before the application of antibodies which are specific to the induced markers.

Identification of Therapeutics:

A further embodiment of the invention is the use of the NSC-specific molecules as targets for pharmacological manipulation of NSCs, neural progenitors, and more differentiated neural cell types, both in vivo and following isolation. Desirable interventions include positive and negative modulation of proliferation and differentiation by identification of agonists and antagonists of NSCs. For example, the agonist may act on a neural stem cell specific marker, thus increasing the growth of the cells. Of particular interest are markers which are either down-regulated or not up-regulated during differentiation of neural stem cells. The method of testing for agonist of NSCs could involve any method known to one of skill in the art, but essentially, the method may involve treating NSCs in vitro or in vivo with a pharmaceutical or other chemical and looking for an increase in number of the NSCs. Antagonists are also of interest for decreasing the growth of NSC or NSC-like cells. These antagonists may act on the cell-specific markers to antagonize growth of NSCs. Of particular interest are markers which are upregulated during the differentiation of NSCs. The method of testing for antagonists would be by treating NSCs in vitro or in vivo with the pharmaceutical or other chemical, and identifying a decrease in the number of NSCs which would identify the chemical as an antagonist.

Examples of methods for the identification of agonists or antagonists are as follows: NSCs are grown in vitro, in tissue culture, to about 50-80% confluency, the chemical or pharmaceutical is then added at various concentrations in the presence of a marker for cell division and the increase or decrease in cell cycling measured relative to control. Alternatively, the NSCs can be grown in vivo and treated before or after in vivo implantation with the chemical or pharmaceutical in the presence of a marker for cell division or cell cycling and the increase or decrease in cell cycling measured relative to control.

A further embodiment of the invention is the use of the NSC-specific molecules before, during, and after isolating undifferentiated neural cell types for use in drug development. Such drugs may have utility as treatments for conditions involving neural stem cells both directly and indirectly, although not always recognized as such. Here we include malignant neoplasms such as glioblastoma multiforme, astrocytoma, and retinoblastoma; infectious diseases such as CMV, rubella, and HIV; inflammatory diseases such as trauma, multiple sclerosis, diabetes, and SLE, as well as neurodestructive and degenerative diseases such as stroke, Parkinson's Disease, Alzheimer's Disease, Huntington's Disease, ALS, retinitis pigmentosa, and macular degeneration. In addition, such drugs may have utility in reducing the overmultiplication of transplanted cells.

Transplantation of NSCs:

A further embodiment of the present invention is the use of NSCs for transplantation into damaged areas of the brain to repopulate the area. Preferably, the NSCs differentiate into the damaged cell type. The cells may also be treated before or after transplantation to be more likely to differentiate into the missing cell type. Such differentiation factors include but are not limited to: Some examples of differentiation agents, include, but are not limited to Interferon gamma, fetal calf serum, nerve growth factor, removal of EGF, removal of bFGF (or both), neurogenin, BDNF, thyroid hormone, BMPs, LIF, sonic hedgehog, GDNFs, VEGFs, interleukins, interferons, SCF, activins, inhibins, chemokines, retinoic acid and CNTF.

Cells having the characteristics of multipotent neural stem cells, neuronal progenitors, and/or glial progenitors of the CNS (identified by in vitro assays) are introduced into a mammal exhibiting a neurological disorder to examine the therapeutic potential of these cells. The cells are preferably isolated from a mammal having similar MHC genotypes or the host mammal could be immunosuppressed using drugs such as cyclosporin A. The cells are injected into the spinal cord, retina or brain. The cells are injected at a range of concentrations to determine the optimal concentration into the desired site. Alternatively, the cells are introduced in a plasma clot or collagen gel to prevent rapid dispersal of cells from the site of injection. The effect of this treatment on the neurological status of the model animal is noted. Desired therapeutic effects in the above mutant mice include the reduction or cessation of seizures or improved movement of lower motor extremities. The cells may be administered using any method known to one of skill in the art. In addition, it is envisioned the new methods will be developed which provide advantages for the various therapeutic treatments or uses of NSCs and RSCs. The NSCs and/or RSCs herein may be administered using the new methods.

Having now generally described the invention, the following examples are offered to illustrate, but not to limit the claimed invention.

EXAMPLES

Example 1 presents that data which was obtained when human NSCs were analyzed for the presence and absence of cell surface markers using a panel of antibodies known in the art (See Table 1).

Example 1

Identification of Positive and Negative Neural Stem Cell Markers in Human Neural Stem Cells Initially, a human neuronal progenitor cell line was obtained from Michael Young, Ph.D. who obtained it from Clonetics, (Walkersville, Md., catalog number CC-2599). These cells had been obtained from donated prenatal tissue and tested negative for a range of infectious pathogens. Cells were obtained frozen and subsequently grown in tissue culture using a defined medium consisting of DMEM/F12 high glucose, N2 Supplement (Life Technologies), bFGF (20-25 ng/ml) and EGF (20-25 ng/ml), and L-glutamine. Cells were characterized as multipotent neural progenitor cells based on the ability to propagate over many passages, expression of nestin and Ki-67, proto-neuronal morphology, as well as the ability to differentiate into neurons and glia (Mizumoto, et al., 2001; Young, et al., unpublished data).

For the present study, cells were initially grown as neurospheres until plentiful, then spheres were broken up and seeded into flasks coated with polyornithine and laminin where the cells grew as an adherent monolayer using the same defined medium described above. After reaching confluence, cells were harvested using Custom ATV (Irvine Scientific), washed in PBS ($Ca^{2+}/Mg^{2+}$ free; Dulbecco's Phosphate Buffered Saline, Gibco BRL, Grand Island, N.Y.) and centrifuged at 400×g for 4 minutes. The resulting pellet was resuspended in PBS using a flame-polished glass Pasteur pipette with a narrow bore. 100 µl of cell suspension, containing approximately $5\times10^5$ cells was distributed among 12×75 polystyrene tubes containing appropriate quantities of listed antibodies. Manufacturers suggested concentrations were observed, with the exception of GD2-FITC in which case 15 µl neat (0.25 mg/ml) was used according to previous experience and titration. Cells were incubated with antibody for 20 minutes at room temperature, protected from light. The cells stained with directly conjugated antibodies were then washed with 2 ml PBS (Dulbecco's Phosphate Buffered Saline, Gibco BRL, Grand Island, N.Y.) and spun at 400×g for 4 minutes, decanted and resuspended in 200 µl of PBS containing 7-amino Actinomycin D (7-AAD) in PBS (1 µg/ml). Following initial incubation and wash, cells incubated with unconjugated antibodies were then stained with FITC goat anti-mouse or PE-conjugated sheep anti-mouse antibody. Unbound antibodies were then removed by washing with 2 ml PBS, as previously described, and resuspended in PBS containing 7-AAD (1 µg/ml). FACS Lysing Soln, (Ammonium Chloride, Tetra Sodium EDTA, Potassium phosphate) was used to ready cells for FACS analysis.

TABLE 1

Antibodies used in the cell surface identification studies

Simultest Control (MsIgG1-FITC/MsIgG2a-PE), BD Biosciences, San Jose, CA.
Ms IgM, κ-FITC Isotype control, BD Biosciences, San Jose, CA
Ms IgG$_1$-PE Isotype control, BD Biosciences, San Jose, CA
Anti-MHC Class I, BD Biosciences, San Jose, CA
β2 microglobulin, BD Biosciences, San Jose, CA
Anti GD2 ganglioside, US Biological, Swampscott, MA
Anti GD3 ganglioside, US Biological, Swampscott, MA
Anti CD9-FITC, BD Biosciences, San Jose, CA
Anti CD15-FITC, BD Biosciences, San Jose, CA
Anti CD34-PE (8G12), BD Biosciences, San Jose, CA
Anti CD56-PE, BD Biosciences, San Jose, CA
Anti CD81, BD Biosciences, San Jose, CA
Anti CD95-PE, BD Biosciences, San Jose, CA
Anti MHC Class II, BD Biosciences, San Jose, CA
Anti HLA-DR PE, BD Biosciences, San Jose, CA
Anti Glycophorin-A, Pharmingen, LaJolla, CA
Anti CD1a, BD Biosciences, San Jose, CA
Anti CD3-FITC, BD Biosciences, San Jose, CA
Anti Zeta-FITC, BD Biosciences, San Jose, CA
Anti CD5-FITC, BD Biosciences, San Jose, CA
Anti CD7-FITC, BD Biosciences, San Jose, CA
Anti CD8-
Anti CD10-FITC, BD Biosciences, San Jose, CA
Anti CD11b-FITC, BD Biosciences, San Jose, CA
Anti CD13-PE, BD Biosciences, San Jose, CA
Anti CD14-FITC, BD Biosciences, San Jose, CA
Anti CD16-FITC, BD Biosciences, San Jose, CA
Anti CD19-PE, BD Biosciences, San Jose, CA
Anti CD20-PE, BD Biosciences, San Jose, CA
Anti CD22-FITC, BD Biosciences, San Jose, CA
Anti CD23-PE, BD Biosciences, San Jose, CA
Anti CD25-PE, BD Biosciences, San Jose, CA
Anti CD31-FITC, BD Biosciences, San Jose, CA
Anti CD33-FITC, BD Biosciences, San Jose, CA
Anti CD34-(epitope 561) and/or Anti CD34 (epitope 8G12)
Anti CD38
Anti CD45-FITC, BD Biosciences, San Jose, CA
Anti CD54-PE, BD Biosciences, San Jose, CA
Anti CD80-FITC, BD Biosciences, San Jose, CA
Anti CD83-PE, BD Biosciences, San Jose, CA
Anti CD86-PE, BD Biosciences, San Jose, CA
Anti CD117-FITC, BD Biosciences, San Jose, CA
Anti CD133
Anit CD152
Anti CD154, BD Biosciences, San Jose, CA Cytometric Evaluation:

The FACS Vantage, equipped with an Enterprise 488 nm argon laser (FACS Vantage cell sorter, BD Biosciences, San Jose, Calif.), was calibrated and aligned using chicken RBC, according to manufacturers directions. Color compensation was preliminarily set using calibrite beads, BD Biosciences, San Jose, Calif. Individual samples were optimized using single positive (CD56) antibody labeling, compared to negative matched isotype controls, for each fluorochrome used. Two color live gating acquisition was used to optimize settings and acquire data. Optimally, 30,000 events were collected and stored electronically for subsequent analysis.

Fluorescence Activated Cell Sorting (FACS):

Cultured hNSCs were combined with human apheresis product and the mixture was labeled with anti-G$_{D2}$-FITC, CD56-PE and CD45 Pe-Cy5. A light scatter gate (R1) was employed to eliminate any possible red blood cells and debris. Gates were then drawn to encompass the CD45 positive (R3) and CD45 negative (R2) populations. Logical gating was used to sort hNSC (R2 and R4) from apheresis product cells (R3 and R5). The two resulting sorted populations were reanalyzed flow-cytometrically to evaluate the efficiency of the sorting procedure.

TABLE 2

Summary of Target Molecules Identified and Eliminated

| | Effect of differentiating conditions: |
|---|---|
| Positive markers: | |
| MHC class I and β2-microglobulin (variable) | No change (except induced by IFN-γ) |
| GD2 ganglioside | Decreases |
| CD8 | |
| CD9 (TM4 superfamily) | Slight decrease |
| CD15 (SLex) | Disappears |
| CD34 (hematopoietic stem cell antigen) (8G12 epitope) | Increases |
| CD34 (561 epitope) | |
| CD38 | |
| CD56 (NCAM) | |
| CD81 (TAPA-1) | |
| CD95 (Fas) | |
| CD152 | |
| Negative markers | |
| MHC class II (DR DQ DP) | No change |
| HLA-DR | |
| Glycophorin-A | |
| GD3 ganglioside (only expressed by small subpopulation) | |
| CD1a | |
| CD3 (TCRαβ-1) | |
| CD3 (TCRξ chain) | No change |
| CD5 | |
| CD7 | No change |
| CD10 | No change |
| CD11b | |
| CD13 | |
| CD14 | |
| CD16 | No change |
| CD19 | |
| CD20 | |
| CD22 | |
| CD23 | |
| CD25 | |
| CD31 | |
| CD33 | |
| CD41 | |
| CD45 | |
| CD54 (ICAM) | Becomes positive with FCS |
| CD80 | |
| CD83 | |
| CD86 | |
| CD133 | |
| CD117 | |
| CD154 | |

A large number of positive and negative markers were identified using this procedure (shown in Table 2). Of special interest was GD2 ganglioside because it was highly expressed by the majority of NSCs (especially as compared to ganglioside GD3 which was only expressed by very few) and because it is a sugar-related marker rather than a protein. In addition, other positive markers of NSCs identified were CD9 (TM4 superfamily) CD15 (LeX), CD34 (hematopoietic stem cell antigen) as tested with antibodies to two epitopes, CD56 (NCAM), CD81 (TAPA-1)CD95 (Fas) and MHC class I and β2-microglobulin.

In direct contrast to the results of Uchida et al. the human neural stem cells which were tested in the present study were CD133−/CD34+. These cells clearly possessed the ability to differentiate into neurons and glia, can be grown as neurospheres, express nestin and Ki-67, and have a proto-neuronal morphology. Thus, the results herein suggest that the method of Uchida et al does not identify the cells known as neural stem cells.

It is envisioned that certain markers would be lost during differentiation of the NSCs and if they are down-regulated during differentiation of the NSCs, they are likely to be very specific NSC markers. In Example 3, the neural stem cells were grown under conditions which induced differentiation and retested for expression of the above markers.

The results now provide supporting evidence that additional positive markers originally identified on human brain derived stem cells (FIG. 1a-i) are consistently expressed by similar cells obtained from a variety of central nervous system (CNS) sources, in this case the brain (FIG. 5) and retina (FIG. 2) of the mouse. In both instances, the additional markers are CD9, CD15, and CD81.

Example 2

Identification of Neural Retinal Cell Markers

Figure 2:
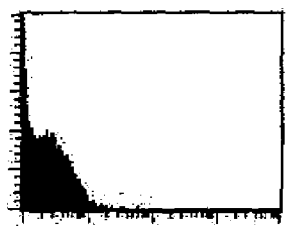
FIG. 2 shows stem cells from the neural retina of GFP-transgenic mice which express the markers previously shown for brain-derived stem cells. 2$a$ is the isotype control, 2$b$ is for GD2 ganglioside, 2$c$ is for CD9 (tetraspanin), 2$d$ is for CD15 (Lewis X, lacto-N-fucopentose III), 2$e$ is for CD81 (tetraspanin).
Figure 2:
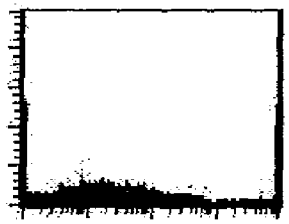
Figure 2:
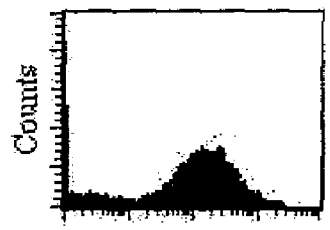
Figure 2:
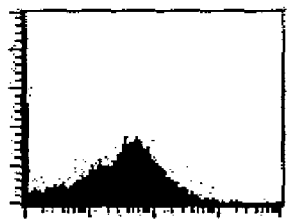
Figure 2:

Stem cells from the neural retina of GFP-transgenic mice were found to express the markers previously shown for brain-derived stem cells. In FIG. 2 the expression of GD2 ganglioside, CD15, and the tetraspanins CD9 and CD81, are shown using flow cytometry.

Example 3

Identification of Neural Cell Markers Associated with Differentiation

Figure 3A:
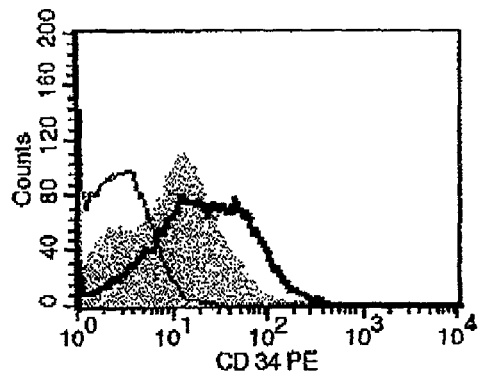
FIG. 3a shows that CD34 expression increases under these conditions (Gray solid line=CD34, Bold outline=CD34 expression following fetal calf serum exposure, Fine outline=isotype control)
Figure 3B:
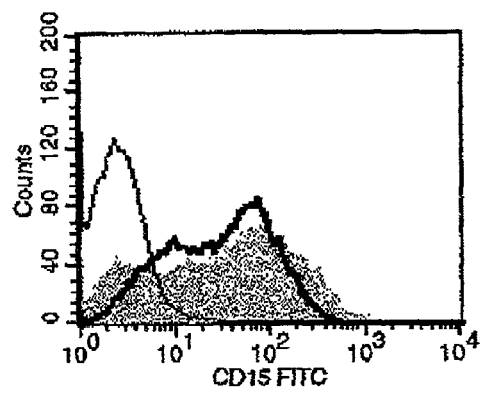
FIG. 3b shows that CD15 expression falls to control levels (Gray solid line=CD15, Bold outline=CD15 expression following fetal calf serum exposure, Fine outline=isotype control)
Figure 3C:
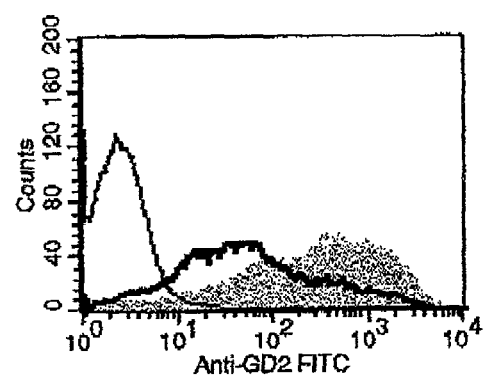
FIG. 3c shows that $G_{D2}$ ganglioside expression decreases by an order of magnitude (Gray solid line=$G_{D2}$ ganglioside, Bold outline=$G_{D2}$ expression following fetal calf serum exposure, Fine outline=isotype control)
Figure 3D:
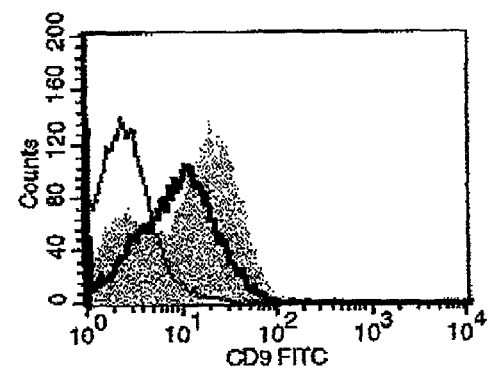
FIG. 3d shows that CD9 expression falls to a lesser degree (Gray solid line=CD9, Bold outline=CD9 expression following fetal calf serum exposure, Fine outline=isotype control).

The human neuronal progenitor cells (hNSCs) in Example 1 were treated with Fetal calf serum (FCS) to induce differentiation and some of the markers were reexamined. FIG. 3 depicts the influence of these differentiating conditions on the expression of target molecules by hNSCs. In each case the target molecule is shown as solid gray, the isotype control with a fine black outline. The bold outline indicates the profile of the target molecule after hNSCs were cultured in fetal bovine serum (FBS). FIG. 3a shows that CD34 expression increased under these conditions, FIG. 3b shows that CD15 expression fell to control levels, FIG. 3c shows that $G_{D2}$ ganglioside expression decreased by an order of magnitude, FIG. 3d shows that CD9 expression fell to a lesser degree.

The expression of certain NSC-specific markers decreased during differentiation, suggesting that these markers are strong markers of "true" neural stem cells. Thus, CD 15 and GD2 are important markers for identifying "true" neural stem cells and CD9 to a lesser degree.

In addition, as the cells differentiated, the level of CD34 actually increased. This was a surprising result and in direct contrast to the work by Uchida et al. which specifically isolated a population of cells which were CD34− as neural stem cells. Thus, the results herein suggest that the population isolated by Uchida et al were either a different population and not "true" neural stem cells, or were a more differentiated version of the neural stem cells identified herein.

Example 4

Expression of Cell Surface Markers During Treatment with IFN-γ

Stem cells from the brain of GFP-transgenic mice did not express class I or class II MHC antigens at baseline or under differentiation conditions. These antigens could, however, be induced by the addition of the cytokine interferon-gamma (IFN-γ), shown in FIG. 4 using flow cytometry. MHC induction by IFN-γ was reversible.

In addition, evidence is provided that expression of some markers differs among neural stem cell populations. Whereas the initial brain-derived line (of human origin) expressed MHC class I surface molecules (FIG. 1b), the subsequent brain and retina-derived lines (from mice) did not. Stem cells from the brain (FIG. 4) and retina of GFP-transgenic mice did not express MHC class I antigens at baseline or under differentiation conditions, although both class I and class II MHC could be induced by IFN gamma. However, many of the same markers are identified on NSCs from mouse brain and retina.

Example 5

Expression of Cell Surface Markers by pNestin-GFP Transgenic Neural Stem Cells

Figure 5:
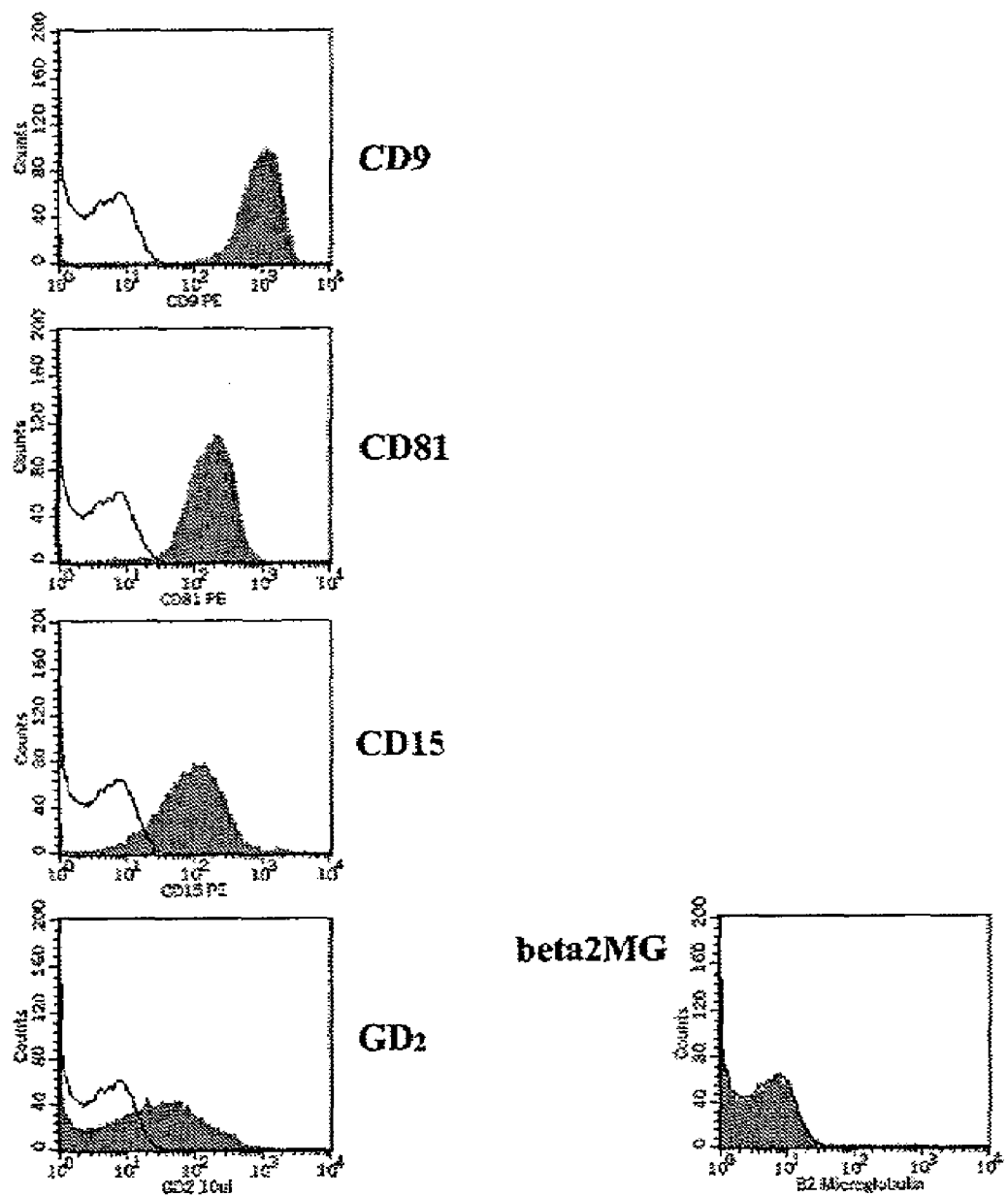
FIG. 5 show flow cytometric documentation of specific markers on conditionally green stem cells derived from the brain of neonatal pNestin-GFP mice. Signal from marker antibody is the shaded curve, from isotype control is open. 5a is CD9, 5b is CD81, 5c is CD15, 5d is $G_{D2}$ ganglioside.

Having documented the presence, or absence, of multiple surface epitopes on human and then mouse brained-derived stem/progenitor cell lines, the analogous cells derived from the brain of neonatal mice transgenic for GFP under the control of the nestin promoter (pNestin-GFP) were analyzed. Analysis was by flow cytometric documentation of specific markers on conditionally green stem cells derived from the brain of neonatal pNestin-GFP mice. In FIG. 5, the signal from the marker antibody is the shaded curve, from isotype control is open. In this figure there was a high expression of the tetraspanin CD9, as well as that of CD81, another tetraspanin (TM4 protein). The Lewis antigen, CD15 was also clearly expressed, as was GD2 ganglioside. In contrast, signal from the MHC class I-associated marker beta-2 microglobulin was indistinguishable from isotype and therefore not expressed.

These results confirmed that the surface marker profile of pNestin-GFPgmBSCs (brain-derived neural stem cells) is quite comparable to that of human neural stem cells, as shown in FIG. 1. These data establish the basis for additional work utilizing these markers in a variety of flow cytometric analyses, including cell sorting.

Example 6

Expression of Cell Surface Markers by pNestin-GFP Transgenic Neural Stem Cells

When flow cytometric evaluation of pNestin-GFP neural stem cells was performed before and after exposure to differentiation conditions, the following was concluded.

Figure 6:
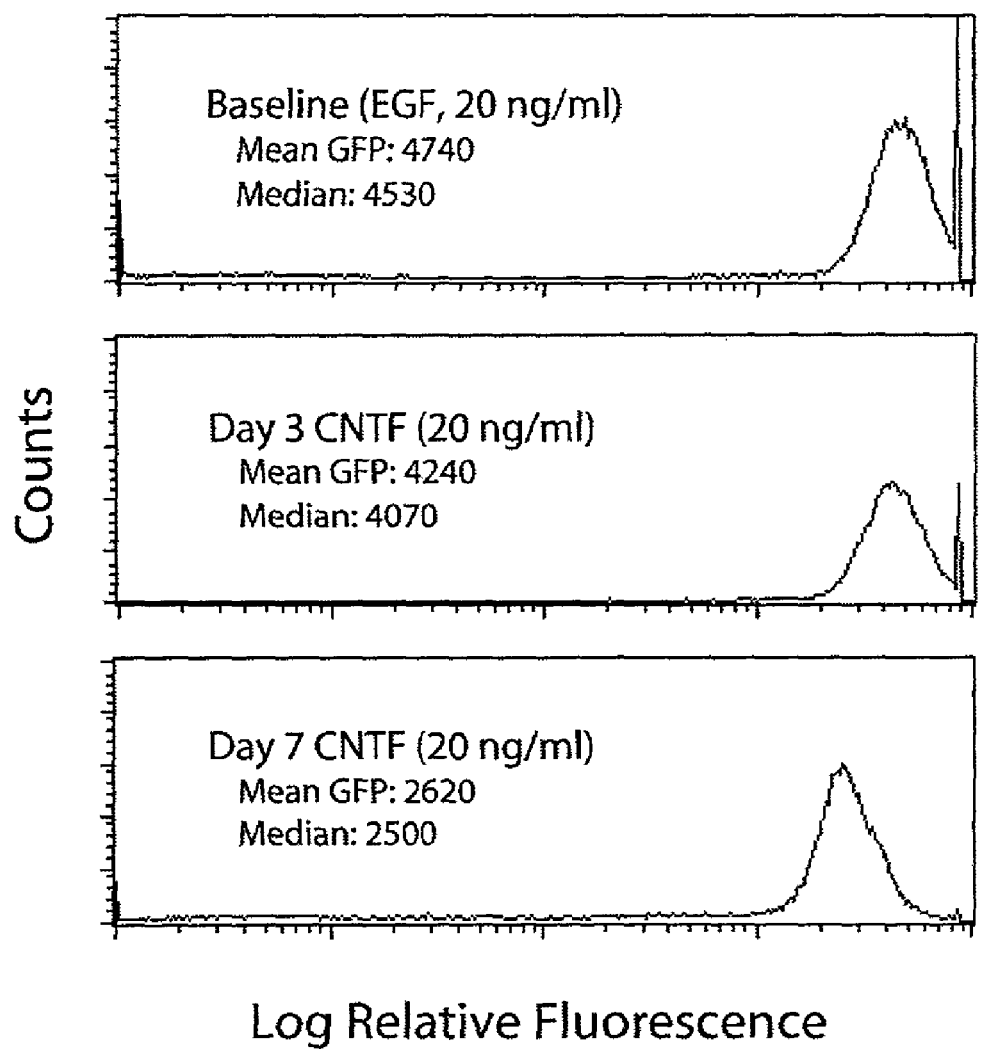
FIG. 6 are flow cytometric evaluations of pNestin-GFP neural stem cells, before and after exposure to differentiation conditions (20 ng/ml CNTF).

In FIG. 6, the top histogram shows the bright endogenous FITC+ fluorescence emitted by pNestin-GFP neural stem cells when cultured under standard proliferation conditions (20 ng/ml EGF). The middle histogram illustrates that there was a modest decrease in endogenous fluorescence (left shift) induced by 3 days of culture under differentiation conditions. The apparent magnitude of this shift is lessened by the log scale of the X-axis, but confirmed by the statistics provided. At bottom can be seen the marked decrease in endogenous fluorescence induced by 7 days of differentiation. In additional work, the changes in GFP expression induced by culturing pNestin-GFPstem cells under differentiation conditions was assessed. In this case, withdrawal from mitogen was used combined with concomitant exposure to CNTF, a factor known to promote astrocytic differentiation. Using unstained pNestin-GFP stem cells and flow cytometry, the fact that these cells exhibit a high level of endogenous FITC+fluorescence under proliferation conditions (EGF, 20 ng/ml) was confirmed. When removed from EGF and cultured in CNTF (20 ng/ml) the level of GFP-associated fluorescence progressively decreased (FIG. D), consistent with down-regulation of nestin expression during differentiation.

Thus, additional data is provided relating the identified surface markers to CNS-derived stem cells. For instance, stem cells were derived from the brains of mice transgenic for GFP under the control of the Nestin promoter. These cells not only expressed GD2 ganglioside, CD9, CD 15, and CD81 (new FIG. 5), but also emitted high levels of baseline FITC+ fluorescence due to conditional expression of the GFP reporter gene (FIG. 6). Endogenous GFP expression by these cells was down-regulated by the addition of the cytokine CNTF, which is known to promote astrocytic differentiation in these cells (FIG. 6). The regulation of GFP expression by these cells is therefore consistent with expression of Nestin, and hence with neural stem cell phenotype. The simultaneous expression of both GFP and the markers GD2 ganglioside, CD9, CD15, and CD81 further supports the idea herein that the latter markers are expressed by neural stem cells.

Example 7

Selected Marker Expression Analysis of Whole Brain Homogenates

Evaluation of selected marker expression by whole brain homogenate was as follows: Mouse brain (pNestin-GFP transgenic) was removed from adult mice, dissociated, and analyzed by flow cytometry. The tetraspanins CD9 and CD81 were found to be highly expressed by a majority of brain cells. CD15 was expressed by many, but not all, brain cells. MHC antigens (FIG. 7*b* IA-d, FIG. 7*c* H2 Kb) were not widely expressed. Of particular note, the GD2 ganglioside (FIG. 7*a*) was not heavily expressed in the brain, despite being prominently expressed by CNS stem cells. This indicates that GD2 ganglioside can be used to prospectively identify and isolate CNS stem cells with good efficiency.

Figure 7:
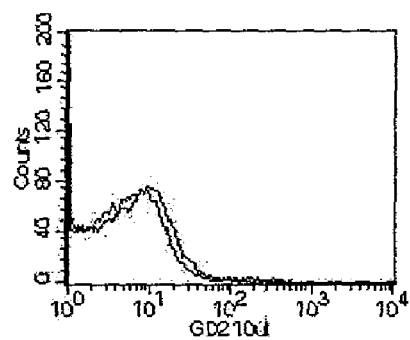
FIG. 7 are an evaluation of selected marker expression by whole brain homogenates. Mouse brain (pNestin-GFP transgenic) was removed from adult mice, dissociated, and analyzed by flow cytometry.
Figure 7:
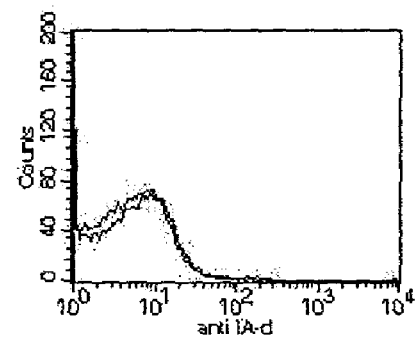
Figure 7:
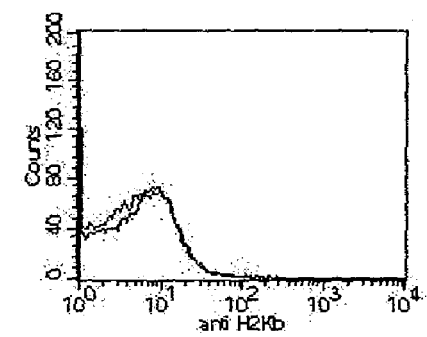

By examining a whole-brain homogenate from pNestin-GFP transgenic mice, a comparison can be made of the expression of these markers between a stem cell population and a whole-brain population (FIG. 7). These data show that whereas GD2 ganglioside is highly expressed on the stem cell population, it is rare on cells of the brain, consistent with the interpretation that GD2 ganglioside provides a selective neural stem cell marker. Expression of CD15 is more widespread in brain, and CD9 and CD81 are both heavily expressed in brain as well as on neural stem cells. Class I and class II MHC antigens are poorly expressed by either.

Example 8

Identification of Positive and Negative Neural Stem Cell Markers in Neural Stem Cells Isolated from Mouse Brain and Retinal Cells.

The mouse neural stem cell lines were generated in the lab of Michael Young, Ph.D. Mouse brain stem cells expressed CD15 and did not express detectable GD3 ganglioside, MHC class I or MHC class II at baseline. Furthermore, the addition of interferon-gamma induced the expression of MHC I and beta-2 microgobulin by the mouse brain stem cell line.

In Example 9, a method for enriching for or isolating NSCs is presented. The method uses the newly identified neural stem cell-specific markers from Examples 1 and 2.

Example 9

Identification and Method of Isolating/Enriching for Neural Stem Cells with Anti-Ganglioside Antibodies The present studies show that the ganglioside $G_{D2}$ is present at high abundance in the cell membrane of the majority of cells comprising the neural progenitor population (See Table 2). This is true across species lines. The presence of $G_{D2}$ has herein been confirmed in a human brain-derived stem cell line (see Example 1) and a mouse brain-derived neural stem cell line (see Example 1), as well as a mouse neural retina-derived stem cell line (see Example 2). In contrast, the ganglioside $G_{D3}$ is expressed, by a small fraction of the human neural progenitor population.

Thus, because neural stem cells express abundant levels of gangliosides, and because ganglioside subtypes are not uniformly distributed across neural cell types during development, anti-ganglioside antibodies (to $G_{D2}$) can be used to generate NSC-enriched fractions from a CNS homogenate or other sample containing mixed cell types.

The use of non-proteinaceous external epitopes for purposes of stem cell isolation represents a novel concept. The fact that gangliosides are not gene products may have contributed to their being overlooked as potential candidates for specific stem cell markers. However one major advantage of using non-proteinaceous markers for isolation and identification of NSCs is that such non-proteinaceous markers have a lack of susceptibility to proteolytic enzymes routinely used during the preparation of tissue for cell harvest. This is important because normal, non-immortalized, neural stem cells require intact growth factor receptors in order to proliferate. Also, because ganglioside molecules are so plentiful within the membrane, antibodies of lower affinity might still be adequate to selectively enrich for NSCs.

Figure 8A:
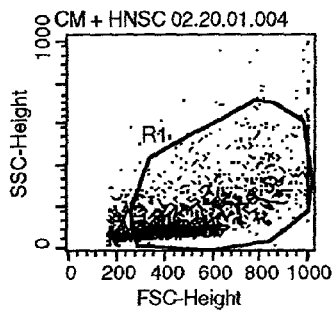
FIG. 8a depicts the light scatter gate (R1) employed to eliminate possible red blood cells and debris.
Figure 8B:
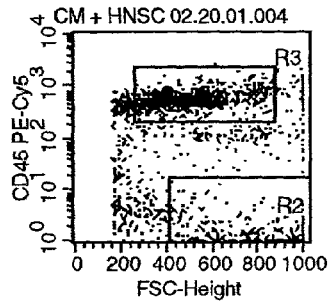
FIG. 8b depicts how gates were then drawn to encompass the CD45 positive (R3) and CD45 negative (R2) populations.
Figure 8C:
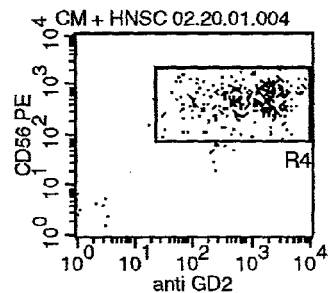
FIGS. 8c-d depict how logical gating was used to sort hNSC (R2 and R4) from apheresis product cells (R3 and R5).
Figure 8D:
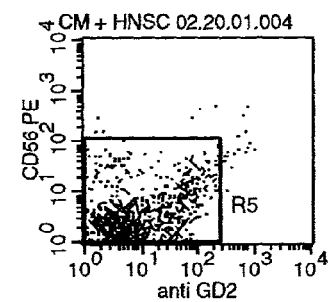
Figure 8E:
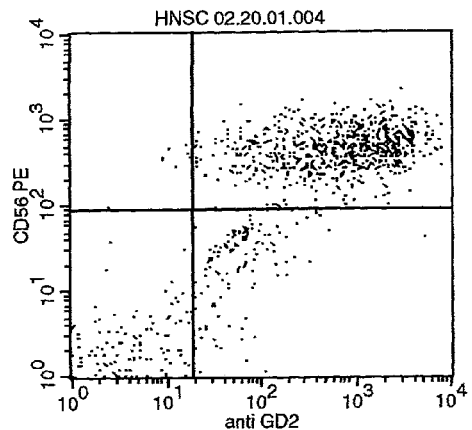
FIGS. 8e-f depict the two resulting sorted populations and demonstrate the efficiency of the sorting procedure.
Figure 8F:
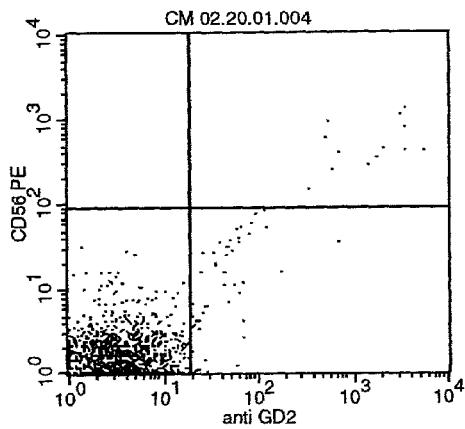

FIGS. 8*a-f* depict the use of anti-$G_{D2}$ ganglioside antibody during fluorescence-activated cell sorting (FACS) to effectively enrich for neural stem cells. Cultured hNSCs were combined with human apheresis product and the mixture was labeled with anti-$G_{D2}$-FITC, CD56-PE and CD45 Pe-Cy5. FIG. 8*a* depicts the light scatter gate (R1) employed to eliminate possible red blood cells and debris. FIG. 8*b* depicts how gates were then drawn to encompass the CD45 positive (R3) and CD45 negative (R2) populations. FIGS. 8*c-d* depict how logical gating was used to sort hNSC (R2 and R4) from apheresis product cells (R3 and R5). FIGS. 8*e-f* depict the two resulting sorted populations and demonstrate the efficiency of the sorting procedure.

For isolating NSCs from fetal/embryonic or adult brain tissue, the following method is used. Fetal/embryonic or adult brain tissue from surgical specimen or post-mortem donation is homogenized and labeled with anti-$G_{D2}$-FITC. The cells are then sorted using FACS. The cells which are $G_{D2}$ positive are collected and further grown in tissue culture or treated and transplanted.

In Example 10, Retinal Stem cells are isolated using essentially the same method.

Example 10

Identification and Method of Isolating/Enriching for Retinal Stem Cells Using Anti-GD2 Ganglioside Antibodies on a Retinal Cells Population The present studies are the first to show that the ganglioside $G_{D2}$ is present at high abundance in the cell membrane of the majority of cells comprising the retinal progenitor population (See Table 2). Therefore GD2 is used to isolate retinal progenitor cells (RSCs) as follows: retinal tissue from a transgenic GFP-mouse, which were propagated and obtained from the lab of Michael Young were labeled with anti-$G_{D2}$-FITC. The cells are then sorted using FACS. The cells which are $G_{D2}$ positive are collected and further grown in tissue culture or treated and transplanted.

RSCs are isolated from fetal/embryonic or adult brain tissue using the following method. Fetal/embryonic or adult retinal tissue from surgical specimen or post-mortem donation is homogenized and labeled with anti-$G_{D2}$-FITC. The cells are then sorted using FACS. The cells which are $G_{D2}$ positive are collected and further grown in tissue culture or treated and transplanted.

Example 11

Method of Isolating/Enriching for Neural Stem Cells Using Positive and Negative Cellular Markers In identifying and isolating neural stem cells, it is advantageous to use a number of different positive and negative markers. Table 2 shows the identification of a large number of positive and negative markers for NSCs, which can be thought of as the "fingerprint" of NCSA's. The following method can be performed using antibodies to one positive neural stem cell marker as set out in Table 2. Alternatively, the method can be performed using two neural stem cell markers, one marker may be positive and one negative or both may be positive or negative markers. It can be envisioned that the more markers that are used, the more likely it is that the desired neural stem cell is isolated.

In one embodiment, GD2 is used as follows: Antibodies to GD2 are used to treat a population of neural stem cells from donated tissue from an adult brain. The antibodies are goat anti-human antibodies. After binding to the cells, the cells are treated with a FITC labeled rabbit anti-goat antibody. Subsequently or concurrently, Antibodies to CD 15 are used to treat the same population of neural stem cells. The antibodies are goat anti-human antibodies. After binding to the cells, the cells are treated with a different FITC labeled rabbit anti-goat antibody. The cells which bound both antibodies are identified as cells having both Fluorescence associated with them by a FACS analyzer. These cells are then combined and grown in tissue culture.

Alternatively, NSCs are isolated using a positive and a negative marker as follows: NSCs are isolated from fetal/embryonic or adult brain tissue using the following method. Fetal/embryonic or adult retinal tissue from surgical specimen or post-mortem donation is homogenized and labeled with anti-$G_{D2}$-FITC, and CD54-PE. The cells are then sorted using FACS. The cells which are $G_{D2}$ positive and CD54 negative are collected and further grown in tissue culture or treated and transplanted.

Alternatively, a plurality of positive and negative markers can be used.

In Example 12, a similar method is used to isolate NSCs from treated or untreated embryonic stem cells.

Example 12

Method of Selecting/Generating/Directing Neural Stem Cells from Embryonic Stem Cells Embryonic stem cells (ES) are non-neuronal, primitive cells which can be induced to form neural stem cells (NSC) by adding specific morphogens. The markers herein can be used to select for NSCs that are a part of the ES population before or after the treatment with a morphogen. Alternatively, the ES can be treated with substances that induce the expression of NSC positive markers or substances that decrease the expression of negative markers to produce NSCs from ES cells. This is because it is believed that ES cells may have to "pass through" a neural stem cell stage to become useful for the treatment of neurological conditions.

Alternatively, other cells may be de-differentiated or transdifferentiated to produce NSCs. For example, recent reports that cells in the skin can become NSC-like, and that fat can become bone, cartilage, or muscle (presumably via conversion to a mesenchymal stem cell-like intermediary) suggest that the neural stem cell specific markers identified herein can be used for directing such transitions.

In Example 13, Antisense oligonucleotides which downregulate Neural stem cell specific markers are used as a therapeutic or research tool.

Example 13

Method of Treating Neural Tumors or Over-Proliferation of NSCs with Antisense to Neural Stem Cell Specific Markers Antisense oligonucleotides are designed which are complementary to the mRNA of positive neural stem cell markers, GD2 and CD15. The antisense oligonucleotides are enclosed into vesicles and administered to the patient with a neural stem cell-derived tumor by injection into the spinal cord. The tumor or overproliferating NSCs are monitored for reduction in the size. Further treatments are administered as needed.

Alternatively, Neural Stem Cells are treated in vitro or in vivo and the effect on multiplication, differentiation and expression of neural stem cell specific genes is monitored.

Example 14 identifies a method of treating neural tumors with antibodies.

Example 14

Method of Treating Neural Tumors or Over-Proliferation of NSCs with Antibodies to Neural cell Specific Markers Antibodies to the positive neural stem cell markers, GD2 and CD15 are produced by recombinant means, hybridoma technology or in an animal model. The antibodies are humanized or used as fragments. The antibodies are fused with a therapeutic molecule such as a chemotherapeutic agent or a toxin. The antibodies are then administered to the patient with a neural stem cell-derived tumor by injection into the spinal cord. The tumor and/or over-proliferating NSCs are monitored for reduction in the size. Further treatments are administered as needed.

Example 15

Method of Blocking MHC Before Transplantation

Figure 4:
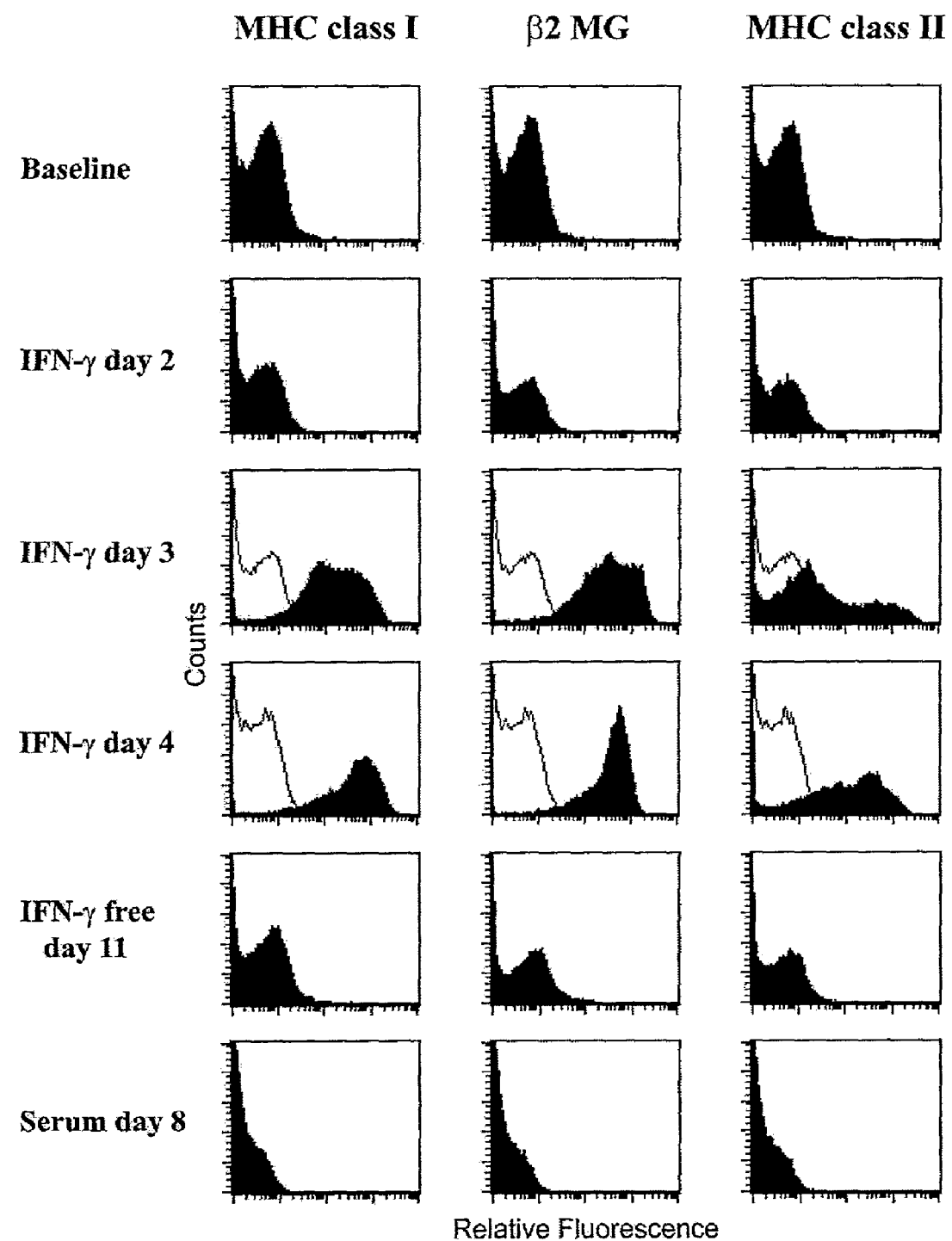
FIG. 4 depicts the induced expression of MHC surface markers in stem cells from the brain of GFP-transgenic mice after treatment with interferon gamma (IFN-γ) for the number of days shown as measured by flow cytometry.

Even when not expressed at baseline, class I and class II MHC antigens could be induced on neural stem cells by treatment with the cytokine interferon-gamma (IFN-γ) and this induction was reversible by cytokine withdrawal (FIG. 4). These observations are of importance, both therapeutically and as a means of prospective identification.

Therapeutically, there could be benefits to blocking certain cytokine receptors on neural stem cells to protect them under pro-inflammatory conditions, particularly as part of stem cell transplantation. Such targets include the IFN-γ receptor, as well as the receptor for the cytokine TNF-α. The use of pharmacological, genetic, or immunological antagonists to these receptors or their expression, or their underlying signaling pathways, could impede induction of MHC expression by stem cells and thus help to protect transplanted stem cells from immunological rejection or apoptosis.

Example 16

Use of MHC for Identification and Selection

Figure 1B:
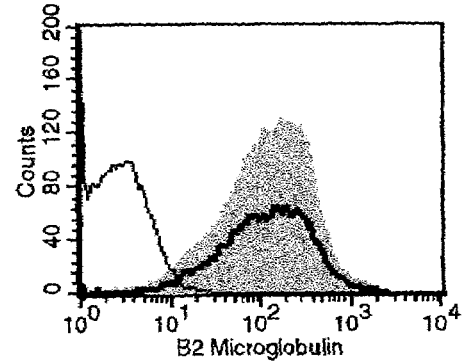
Figure 1C:
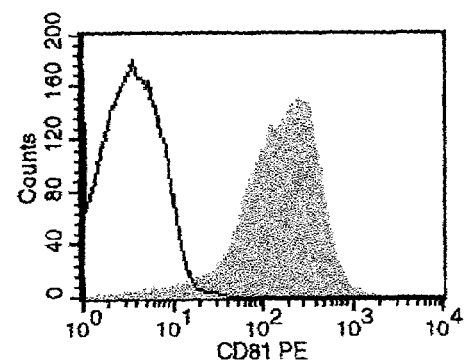
Figure 1D:
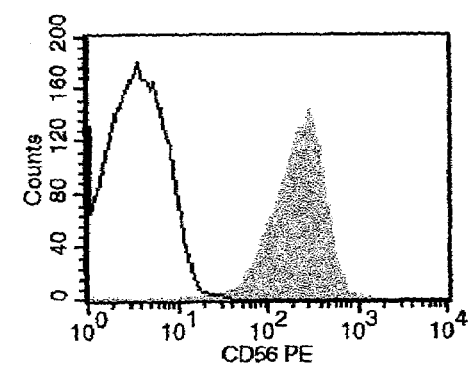
Figure 1E:
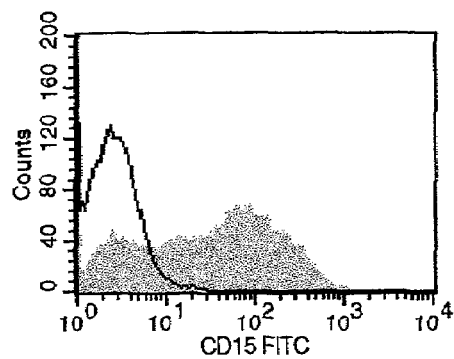
Figure 1F:
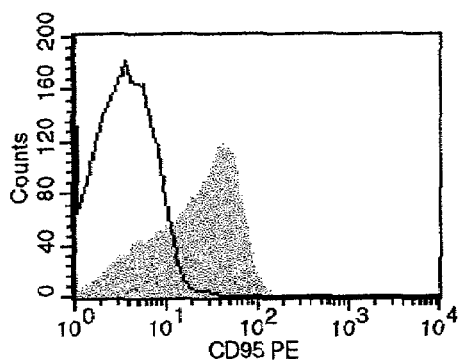
Figure 1G:
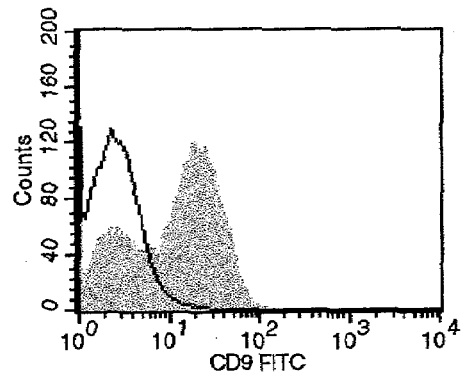
Figure 1H:
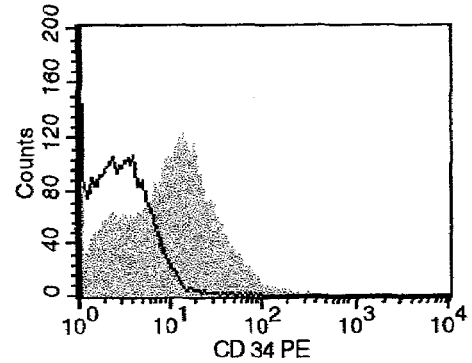
Figure 1I:
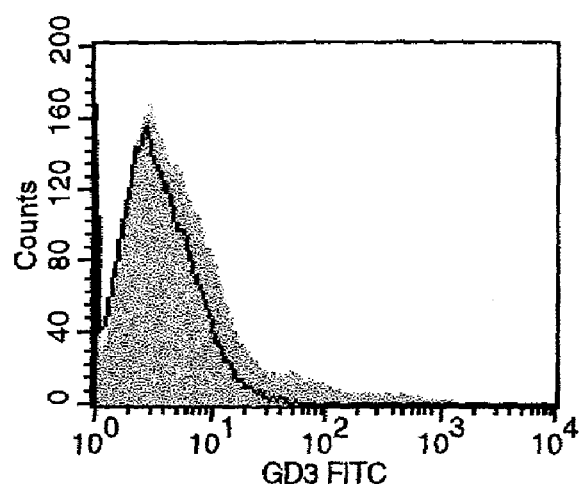
Figure 1J:
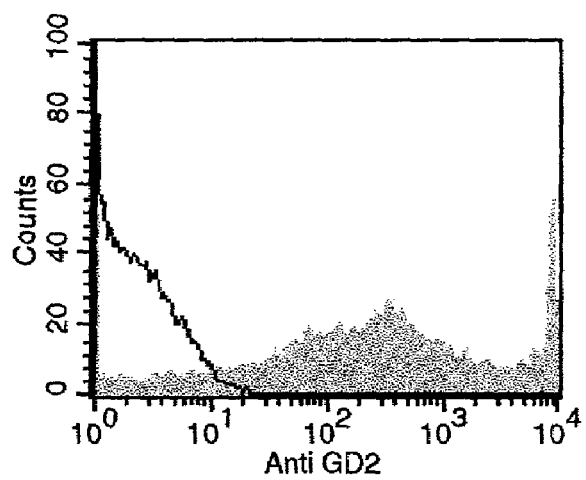
Figure 1K:
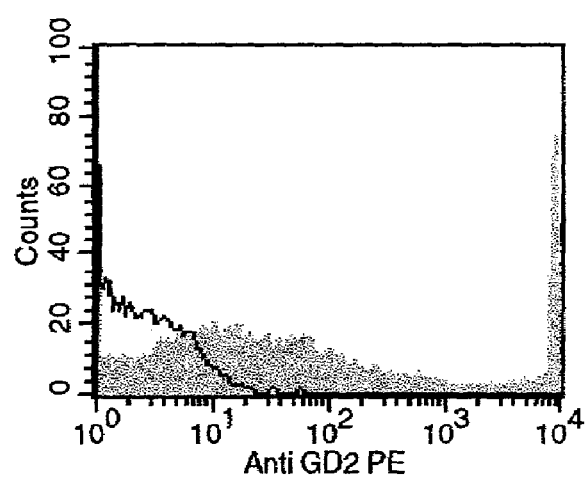

The reversible induction of MHC expression by neural stem cells may be used as a means of prospective identification and selection of these cells within a mixed CNS population as follows:

The method takes advantage of the fact that MHC molecules contain bound peptide fragments of intracellular proteins. These fragments serve as epitopes as part of normal immune function. Whereas it has been known that neural stem cells contain relatively specific intracellular markers, these have not been useful for prospective identification and selection because these epitopes are sequestered internally and not accessible for antibody binding without first killing the cells. In addition, although MHC-bound fragments of intracellular proteins represent external epitopes on the surface of MHC-bearing cells, MHC expression tends to be low-to-absent on resident cells of the CNS, including neurons, astrocytes, and oligodendrocytes of the brain, retina, and spinal cord. Furthermore, the data presented in the current application indicates that MHC expression by neural stem cells is frequently quite low, although this expression can vary considerably (FIGS. 4 and 1*b*).

The method uses the MHC-bound fragments of intracellular stem cell markers as epitopes for purposes of prospective identification and selection of these cells. An example of such a marker is the cytoskeletal protein Nestin. Examples of other markers include MASH 1 and Musashi 1 (MSI 1). When MHC molecules are not present on a stem cell population, they are transiently induced by the addition of MHC-inducing agents such as the cytokines IFN-γ or TNF-α. These are added ex vivo to a CNS tissue homogenate or, where appropriate, to the intact organism prior to harvesting.

Following induction, the CNS tissue homogenate is exposed to ligands which specifically bind to epitopes formed by fragments of intracellular stem cell markers. Examples of these ligands include, but are not limited to, immunological molecules such as monoclonal or polyclonal antibodies, or T cell receptors, or modified versions of such molecules. Following selection, the bound cells are eluted and cultured in growth medium in the absence of MHC-inducing agents. The MHC expression is temporary, so that after culture, the cells may be transplanted into a mammal.

In Example 17, a method of transplanting the NSCs of the preferred embodiment is presented.

Example 17

Method of Transplanting Neural Stem Cells of the Preferred Embodiment

Cells having the characteristics of multipotent neural stem cells, neuronal progenitors, or glial progenitors of the CNS (identified by in vitro assays) are introduced into a mammal exhibiting a neurological disorder to examine the therapeutic potential of these cells. The cells are preferably isolated from a mammal having similar MHC genotypes or the host mammal is immunosuppressed using drugs such as cyclosporin A. The cells are injected into the spinal cord or brain. The cells are injected at a range of concentrations to determine the optimal concentration into the desired site. Alternatively, the cells are introduced in a plasma clot or collagen gel to prevent rapid dispersal of cells from the site of injection. The effect of this treatment on the neurological status of the model animal is noted. Desired therapeutic effects in the above mutant mice include the reduction or cessation of seizures or improved movement of lower motor extremities.

In Example 18, a method for treating the excessive proliferation of neural transplants is presented.

Example 18

Method of Treating Excessive Proliferation of Neural Transplants

A patient who has received a neural stem cell transplant which is over-proliferating is identified. The antisense oligonucleotide of Example 13 or the antibodies of Example 14 are administered to the patient who has received a neural stem cell transplant in an amount effective to reduce the overgrowth of the transplant, but not so much as to kill the transplanted cells. The patient is monitored and further treatments are administered as needed.

In Example 19, a method for the treatment of Parkinson's Disease using the NSCs of the preferred embodiment is presented.

Example 19

Method of Treating Parkinson's Disease

Sufficient cells for grafting (assuming a 20% viability) are isolated using the method of Example 9 or 11. The cells are then transplanted into the striatum or the substantia nigra using the method of Example 17. The transplant is monitored for viability and differentiation of the cells. Further treatments are included as needed.

Although any of the positive markers for brain-derived stem cells (FIG. 1 *a-j*) and could be used for isolating these cells, the following example uses GD2 ganglioside which is also present on (mouse) retinal stem cells (RSCs).

Example 20

A Method for Sorting of Cells Using the GD2 Cell Surface Marker

Figure 9:
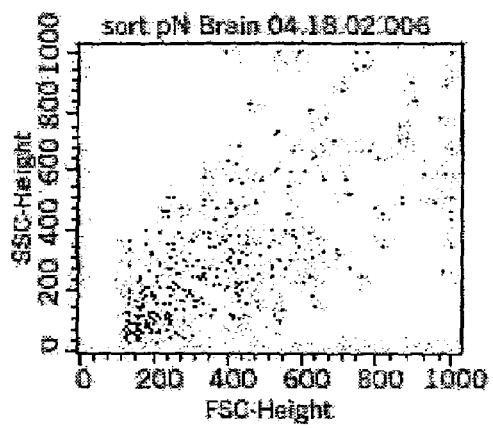
FIG. 9 depicts the isolation of GD2+ stem cells from whole brain homogenate from adult mice.
Figure 9:
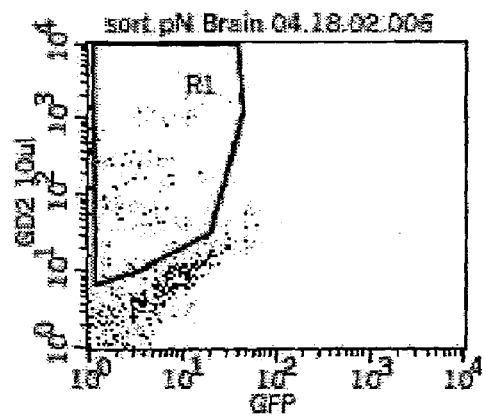
Figure 9:
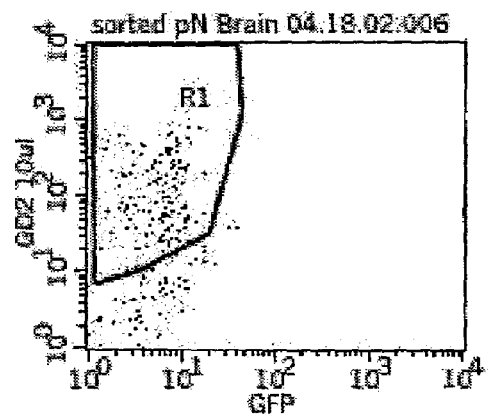

Whole brain homogenate from adult mice was incubated with anti-GD2 primary antibody and PE-conjugated secondary antibody and then sorted by FACS to select for GD2+ cells. FIGS. 9*a-c* depict the isolation of GD2+ stem cells from whole brain homogenate from adult mice. FIG. 9*a* shows whole brain homogenate which was incubated with anti-GD2 primary antibody and PE conjugated secondary antibody, then sorted by FACS to select for GD2+ cells. FIG. 9*b* depicts the initial GD2 population labeled R1 which was 10.9%. FIG. 9*c* depicts the resulting sorted population which was 71% GD2+ representing an enrichment of approximately 700%.

These results demonstrate that GD2+ cells, a relatively small subpopulation of brain cells, can be effectively identified and selected using fluorescence activated cell sorting (FACS). By eliminating the majority of GD2− brain cells, the resulting sorted population is enriched for neural stem cells.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. A method for enriching for neural stem cells or a more restricted subset of progenitors, comprising:
   identifying cells with a positive neural stem cell marker from a population of cells; and
   enriching said cells for cells having said positive neural stem cell marker, wherein said positive neural stem cell marker is CD15, thereby obtaining a population of cells enriched for neural stem cells (NSCs) or a subset of progenitors of neural cells more restricted than NSCs.

2. The method of claim 1 wherein said enriching for cells with a neural stem cell marker is by cell sorting.

3. The method of claim 1 wherein said enriching for cells is with a neural stem cell marker by using an affinity column.

4. The method of claim 1 wherein said population of cells is from a tissue selected from the group consisting of: the brain, the spinal cord, the retina, and fetal tissue.

5. The method of claim 4, wherein said brain and retina are adult brain and retina.

6. The method of claim 1, wherein the obtained population of cells is CD 133−.

7. The method of claim 1, wherein the obtained population of cells is CD133+.

* * * * *